United States Patent [19]
Sirén

[11] Patent Number: 6,153,603
[45] Date of Patent: Nov. 28, 2000

[54] METHOD OF TREATING ANGIOGENESIS IN TUMOR TISSUE

[75] Inventor: Matti Sirén, Snellmansgatan, Finland

[73] Assignee: Perstorp AB, Perstorp, Sweden

[21] Appl. No.: 09/093,074

[22] Filed: May 22, 1998

Related U.S. Application Data

[63] Continuation-in-part of application No. 08/860,511, Jun. 27, 1997, abandoned.

[51] Int. Cl.$^7$ .................................................. A61K 31/66
[52] U.S. Cl. ................................................. 514/102
[58] Field of Search ............................................ 514/102

[56] References Cited

U.S. PATENT DOCUMENTS

| | | | |
|---|---|---|---|
| 4,590,060 | 5/1986 | Ehrenfeld | 514/102 |
| 4,952,396 | 8/1990 | Sabin et al. | 514/102 |

*Primary Examiner*—Jerome D. Goldberg
*Attorney, Agent, or Firm*—Stevens, Davis, Miller & Mosher, L.L.P.

[57] ABSTRACT

The present invention relates to a method of treating angiogenesis in tumor tissue, such as glioma and glioblastama tissue. The method comprises administering to a mammal, including, man an effective amount at an isomer of inositol trisphosphate, such as D-myo-inositol-1,2,6-trisphosphate, or a pharmaceutically acceptable salt thereof.

12 Claims, No Drawings

METHOD OF TREATING ANGIOGENESIS IN TUMOR TISSUE

This application is a continuation-in-part of prior application Ser. No. 08/860,511, filed Jun. 27, 1997, now abandoned.

The present invention relates to a method of treating angionesis in tumor tissue, which method comprises administering an isomer of inositoltrisphosphate ($IP_3$) or a pharmaceutically acceptable salt thereof.

Even as early as the year 1900, different researchers had reported the finding of the organic phosphate compound phytic acid, that is 1,2,3,4,5,6-myo-inositol-hexakis (dihydrogen phosphate) in plants. The content of phytic acid in different plants varies considerably.

In the literature there are reports on the presence of inositol pentaphosphate and inositol tetraphosphate in a few plants. It is furthermore known that inositol phosphate derivatives with less phosphate groups than phytic acid are formed during germination of grain. For instance, the final products during germination are inositol and phosphate.

The use of phytic acid or its salts, phytates, has been described in several scientific publications. The majority of the authors of these articles have observed several negative effects in humans or animals when consuming phytic acid or its salts or compounds containing the same. For example, feeding dogs with too high an amount of phytic acid gives rise to rachitis. In humans lack of zinc and as a consequence thereof slower growth of children has been observed after consumption of diets with phytic acid or phytates. Because of the above mentioned negative effects on the mineral balance in humans and animals, attempts have so far been made to reduce the intake of phytic acid or phytates to a minimum.

Tumor diseases may be defined as a progressive series of genetic events which occur in a single clone of cells as a result of alterations in a limited number of specific genes, that is oncogenes and tumor suppressor genes. Consistent chromosome aberrations are observed for example in lung, colon, and breast cancers. In this manner tumor diseases can be understood as a result of the accumulation of multiple genetic changes (E. Solomon et al., Science, 254, 1153–1160, 1991).

One severe type of tumor diseases are brain tumors or gliomas. In humans, gliomas account for over 60% of primary intracranial neoplasms. Most commonly, gliomas arise from malignant transformations of astrocytes and according to histopathological criteria they are classified as astrocytoma (low grade glioma or glioblastoma, or high grade glioma). A glioblastoma is a tumor characterized by high cell density, cellular polymorphism, mitoses, necroses with palisading cells and prominent vascularisation with endothelial cell proliferation. Glioblastoma is often seen as the prototypical tumor when developing new therapeutical regimes.

The progressive in vivo growth of malignant tumor cells within a tumor tissue, becomes possible only after the formation of an adequate blood supply system within said tumor tissue. Such a system is formed by the incorporation of existing host vessels into the tumor tissue as well as by the creation of new tumor microvessels. The vasculature network in human cancers is essential for the existence of these malignant tissue systems. The tumor vasculature network provides cancer cells with vital nutrients and also enables the removal of waste products generated by the cells. The vascularization of a tumor tissue also influences positively the proliferation of tumor cells. For example, tumor cells in the vicinity of blood vessels have a greater growth rate than those tumor cells which are located further away from blood vessels.

Angiogenesis is a central part of the process of blood vessel formation. In normal physiological activities, including reproduction and tissue development, angiogenesis is highly regulated as it is activated for only brief periods and then completely inhibited. In many diseases, however, the regulation of angiogenic activity is loosened. In some cases angiogenic activity becomes completely unregulated and its rate is exhilarated.

Angiogenic activity is central to the proliferation of tumor cells in a human body. The often rapid development of new blood vessels through angiogenesis provides a highly effective means for this process. The new blood vessels become a gateway through which tumor cells enter the human circulatory system and eventually metastasize into distant sites such as the liver, lungs, bones, etc. (J. Folkman, Y. Shing; J. Biol. Chem., 267, 10931–10934, 1992).

When a healthy cell is on the borderline of becoming a malignant tumor cell, the tissue which surrounds the cell must induce angiogenic vessel formation in order to attract the nourishing vasculature which the developing cells need for their growth. In such cases angiogenesis is controlled by a balance between local factors which on the one hand stimulate vasculature growth and on the other inhibit vasculature growth. In most normal tissues, the inhibitory influences of the local factors predominate the angiogenic process, and cells which are derived from such tissues generally do not stimulate angiogenesis.

In many pathological conditions, however, diseases appear to be driven by and spread through unregulated angiogenesis. A primary example of such abnormal, unregulated angiogenic activity is the proliferation and metastasis of solid tumors.

An in vivo tumor is formed only when the host produces a stroma and the vascular network which is required for the survival and growth of the neoplastic cell population.

The stroma consists of (a) provisional fibrin gel matrix, (b) new blood vessels, (c) inflammatory cells, (d) connective tissue. Malignant growth has been shown to depend in general on complex interactions between the tumor and the immune and homeostatic systems.

The growth of solid tumors beyond microscopic clumps of cells requires the development of a vascular network which provides the malignant cells with nutrients and oxygen. The additional nutrients and oxygen supplied through the new vasculature allows dysplastic growth of the transformed cell populations, this in turn promotes further vessel development. Differentiation, mutation, and selection of tumor cells occurs throughout this cycle, and the formation of three-dimensional tumors is the ultimate result of the process. Such tumors may be locally invasive, metastatic or both.

A continuous remodelling of the tumor extra-cellular matrix controlled by malignant cells which are characterized by different degrees of biosynthesis and degradation, has been observed during the development of primary and metastatic tumors (Iozzo, R.V. and Cohen, I., 1993; Dvorak, H.F. et al, 1992).

Abnormal accumulation of fluid typically accompanies solid, and particularly ascites tumor growth. The formation of ascites fluids is made possible by rapidly increasing microvascular permeability. Observations made in experimental animal studies as well as clinical human studies indicate that accumulation of ascites fluid can be attributed to alterations in the permeability of the vessels which form the lining for the peritoneum and other cavities. The vessels which form the lining for the peritoneal cavity in ascites tumor bearing guinea pigs, hamsters, and mice manifest significantly greater permeability than similar vessels in control animals. Secretion of permeability increasing activity appears to be a common feature in tumor tissue and may contribute to the abnormal accumulation of fluid in neoplastic diseases.

All tumor tissue, solid or otherwise compact, consists of different types of cells, never of individual cells living in isolated environments.

Tumor diseases comprises more than one hundred different diseases. Each of these has between two and four stages and each can be divided into smaller, more or less critical, subtypes based on histological criteria and enzymological and other findings. All of the different stages and subsets are potential targets for therapeutic treatment and combinations thereof. Such treatments include chemotherapy, hormone therapy, radiotherapy, cytokine therapy, and surgery.

It is significant to note that even though the term "chemotherapy" is generally used to denote the application of cytotoxic agents, the term actually refers to over 30 quite different cytotoxic agents all of which are in common clinical use. It is also important to keep in mind that when cytotoxic agents are administered alone or in combination with one another they have extremely steep dose response curves. Because the dose and response curves of most cytotoxic drugs coincide with their toxicity and efficacy level curves, in therapy most of these agents are applied at doses which are close to their maximum level of tolerance. As a result, the harmful side effects of cytotoxic drugs are difficult to avoid. Discrepancies in the drug metabolism and doseresponse relationship of individual partients make the situation even more problematic.

During the past decades cytotoxic drugs have become increasingly popular as a treatment for neoplastic diseases and they have become invaluable for clinical cancer therapy. In order to combat the heterogeneity of the variable tumor cell metabolism of the neoplastic cell population, many of these therapeutic agents are frequently used in combinations with one another. In cancer chemotherapy such polypharmacy has become almost a rule. Today it is also clear that many anti-cancer drugs are essentially prodrugs which require metabolic activation in order to exert their selective cytotoxic effects.

Many cytotoxic agents are not very selective in terms of their target cells, meaning they are cytotoxic also towards normal, healthy cells. Antineoplastic drug therapy treatments function selectively by targeting rapidly dividing cells. However, clinical experience shows that many, curable cancers grow at a relatively slow rate whereas many treatment resistant cancers are quite rapidly spreading.

Recent research seems to suggest that one of the most significant effects of antineoplastic drugs is the induction of apoptosis in tumor cells. Apoptosis is a genetically encoded and activated cell death program which is defined by specific morphological and biochemical changes within a cell. A multitude of factors regulate apoptosis induction; these include, for example, intracellular mediators of signal transduction, the modulation of gene expression by nuclear proteins, DNA replication, and the cell cycle.

Another approach for curing tumor diseases has been to develop angiosuppresive agents. However, almost all potential angiosuppresive agents have proven to be too toxic for clinical use as their tolerability in humans generally are too low.

The primary focus of cancer research is the individual cancer cell and its metabolism. However, the symbiotic relationship of a cancer cell and its surrounding environment has escaped critical attention.

To summarize there is a need for a new and effective anti-tumor agent without harmful side effects as disclosed and discussed above. A new anti-tumor agent should not be a cytostatica, because the aim is not the destruction of a single tumor cell, but instead the blocking of the tumor tissue growth mechanism and it must be able to prevent the angiogenesis of tumor tissue.

According to the present invention it has quite surprisingly become possible to use an isomer of inositoltrisphosphate ($IP_3$) for treatment of angionenesis in tumor tissue.

The $IP_3$ of the present invention is effective in treatment of angiogenesis related to glioma, glioblastoma, sarcoma such as Kaposi sarcoma, prostate carcinoma, colon adenocarcinoma, pancreas carcinoma, mamma adenocarcinoma, lung carcinoma, such as small cell lung carcinoma, human histiocytic lymphoma and melanoma. Said $IP_3$ exerts significant effect without side effects which is very beneficial for a patient.

Production of $IP_3$ and isolation of the different isomers thereof are disclosed in U.S. Pat. No. 4,777,134. The $IP_3$ isomers can also be produced by synthetic methods, chemically or enzymatically, starting with for instance inositol and a phosphorus source. Furthermore, microbiological production methods, including hybrid DNA-techniques of $IP_3$ are also suitable.

The structure of $IP_3$ and the different isomers thereof are disclosed in U.S. Pat. No. 4,735,936 and the U.S. Pat. No. 4,797,390.

From the European Patent No. 179439 a pharmaceutical composition comprising as a pharmaceutically active ingredient at least one isomer of inositoltrisphosphate is known. In said patent the effect of this pharmaceutical composition is shown for different areas, such as platelet aggregation.

U.S. Pat. No. 4,473,563 discloses extracorporal treatment of erythrocytes to incorporate therein inositol phosphates to improve the oxygen supply. The erythrocytes are separated from blood which has been pumped out of the body for that purpose. After a complicated procedure the erythrocytes are re-introduced into the blood. There is no disclosure of administering inositol phosphates directly to the body.

In U.S. Pat. No. 2,723,938 the use of inositol phosphates is disclosed for stabilising dispersions of an aqueous suspension of penicillin after prolonged storage. This ensures that brief and simple manual shaking will restore a state of complete dispersion of the penicillin after prolonged storage.

Medical applications of phytic acid has been suggested, for example as an antidote for toxic metal absorption, for reducing calcium concentration in urine and to reduce the incidence of dental caries.

U.S. Pat. No. 4,952,396 discloses a method for inhibiting tumour growth by the use of phytic acid, phytate salts and hydrolysates thereof. The efficacy of the treatment is described to be reached by a combining a phytate treatment with a low calcium diet. In general oral administration of 2 to 4 grams of phytic acid per kilogram is described which for a person with a body weight of 70 kg means daily intake of between 140 and 280 gram. Such an intake would correspond to between one third and one half of the total daily intake of diet which, by obvious reasons, is not possible to adhere to in practice.

Furthermore, hydrolysates of phytic acid or phytate salts are being described to be included in the invention of U.S.

Pat. No. 4,952,396. A hydrolysate of phytic acid or a phytate will comprise a mixture of inositol, mono, di, tri, tetra, penta and hexaphosphorylated inositols. Only out of myo-inositol phosphates there are more than 50 different isomers which can be formed. In addition to this there exists another eight different isomers of inositol such as chiro, muco, scyllo etc. which renders a very large amount of different compounds in a hydrolysate of phytic acid or a phytate. Such a mixture will not be pharmaceutically acceptable and no medical authority such as FDA would allow the administration of such a mixture to humans. Neither would any physician allow a treatment with such a mixture before a complete description of the safety aspects of every compound in the mixture was shown. Although this description, the prior art is not disclosing any method of preventing, alleviating, combatting or treating angiogenesis in tumour tissue by administering a specific isomer of $IP_3$ or a pharmaceutically acceptable salt thereof.

It is suitable that the isomer of $IP_3$ used according to the invention exists in a unit dosage form. Tablets, granules or capsules are suitable administration forms for such a unit dosage. Furthermore, tablets and granules can easily be surface treated to provide an enteric coating preventing uncontrolled hydrolysis in the stomach and bringing about a desired absorption in the intestine. Other suitable administration forms are slow release and transdermal administration. A usual pharmaceutically acceptable additive, excipient and/or carrier can be included in a medicament comprising the $IP_3$ isomer. Tablets or granules can also contain a disintegrant which causes the tablets or the granules, respectively, to disintegrate easily in the intestine. In certain cases, especially in acute situations, it is preferable to use the unit dosage in the form of a solution for intravenous administration. In other situations can suspensions comprising the compound preferably be used as administration form.

The method of the present invention can comprise administering one or more specific IP3 isomers, each present in substantially pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

It is in most cases suitable that the isomer of $IP_3$, used according to the method of the invention, is present in salt form in order not to affect the mineral balance negatively. The salt should preferably consist of a sodium, potassium, calcium, zinc or magnesium salt or a mixture of two or more of these salts.

It is also and for the same reasons as above an advantage if the isomer of $IP_3$ is administered together with a surplus or an extra addition of at least one pharmaceutically acceptable salt of calcium, zinc or magnesium with a mineral or organic acid. This is especially valuable for elderly persons who often are deficient in these minerals.

The appropriate administration dosages for man can routinely be determined by those skilled in the art by extension of the results obtained in animals at various dosages. The preferred dosage for man falls within the range of 0.1 to 1000 mg, especially 0.1–200 mg $IP_3$/day/kg body weight.

In animal experiments, no toxic effects were seen after administration of very high doses of $IP_3$, 160 mg/kg body weight, by intraperitoneal injection to mice. Said unit dosages usually comprise 0.01–1.5 g, such as 0.05–1.3 g or preferably 0.1–1 g of $IP_3$.

The most preferred isomers of $IP_3$ include:
D-myo-inositol-1,2,6-trisphosphate of formula

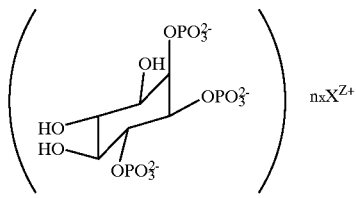

wherein X is hydrogen, at least one univalent, divalent or multivalent cation, or a mixture thereof, n is the number of ions, and z is the charge of the respective ion;
Myo-inositol-1,2,3-trisphosphate of formula

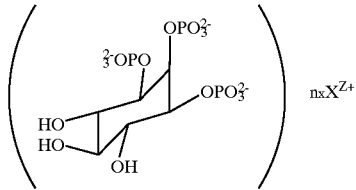

wherein X, n and z have above mentioned meaning;
L-myo-inositol-1,3,4-trisphosphate of formula

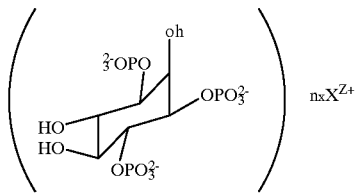

wherein X, n and z have above meaning.

In each of the formulas above n ranges between 6 and 1 inclusive and z ranges from 1 to 6 inclusive. Preferably, n is between 3 and 6 inclusive and z is 3, 2 or 1.

Further isomers of $IP_3$ that may be utilized in the present invention have the structural formula

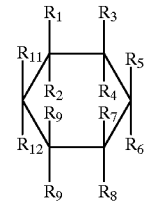

One group of inositol trisphosphates is defined by structural formula (I) wherein three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol trisphosphates is defined by the structural formula (I) wherein three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol trisphosphates is defined by the structural formula (I) wherein three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol trisphosphates is defined by the structural formula (I) wherein three of $R_1$, $R_4$, $R_5$, $R_8$, $R_9$ and $R_{12}$ are hydroxyl and the remaining three are phosphate and $R_2$, $R_3$, $R_6$, $R_7$, $R_{19}$ and $R_{11}$ are hydrogen.

Still yet another group of inositol trisphosphates is defined by the structural formula (I) wherein three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol trisphosphates is defined by the structural formula (I) wherein three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol trisphosphates is defined by the structural formula (I) wherein three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol trisphosphates is defined by the structural formula (I) wherein three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol trisphosphates within the contemplation of the above formula include compounds having the structural formula (I) wherein $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_3$, $R_5$ and $R_9$ are phosphate, $R_1$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

Above formula describes specific isomers of inositol trisphosphate where the inositol is selected from the group consisting of myo-inositol, cis-inositol, epi-inositol, allo-inositol, neo-inositol, muco-inositol, chiro-inositol and scyllo-inositol. The invention will be further explained in attached examples without limitation it thereto. Example 1 shows preparation of a solution of $IP_3$ for intravenous administration and Example 2 illustrates the effect of $IP_3$ on glioma tumor tissue in nude mice. Nude mice have been used extensively for the transplantation and propagation of human xenografts in order to design adequate in vivo experiments with high correlation to effects in the human body.

In order to further increase the prediction of animal experiments for situations in the human body the severe combined immunodeficient mouse (SCID) has been used as this animal allows heterotransplantation of human tumors. Example 3 demonstrates the effect of $IP_3$ in a prostate tumor experiment and example 4 shows the antiangiogenetic effect of $IP_3$ in a lung tumor experiment.

EXAMPLE 1

Solution of the sodium salt of D-myo-inositol-1,2,6-trisphosphate ($IP_3$) for injection.

0.5 g of the sodium salt of $IP_3$ and 0.77 g of sodium chloride were dissolved in 98.73 ml of water for injection to form a solution suitable for injection into a person or an animal.

EXAMPLE 2

Rat glial cells were grown in a stationary suspension culture in a medium supplemented with 15% of heat inactivated horse serum and 2.5% of heat inactivated fetal calf serum in a 5% $CO_2$ humidified atmosphere at 37° C.

The cells were harvested using trypsine solution and the concentration of cells were measured. The cells were centrifuged and resuspended to a concentration of 1 million cells/ml.

Twelve female specific pathogen free mice at an age of 12 weeks (weighing 20–25 g) were maintained in autoclaved cages with filter tops in horizontal air flow cabiners in a unit equipped with specific filters. Autoclaved bedding, irradiated feed and sterile water were used. The temperature and humidity were kept constant at 22±2° C., 65±5% relative humidity.

To each animal 0.1 ml of the cellsuspension was inoculated subcutanousely in the right flank at day 0.

After five days, osmotic minipumps (ALZET) were surgically placed subcutanously into 7 animals, while 5 animals, sham operated, served as a control group.

Each minipump contained approximately 200 μl of a solution of 1.0 g/2.5 ml of the sodium salt of 1-D-myo-inositol-1,2,6-trisphosphate ($IP_3$). The minipumps gave a continous dosage of $IP_3$ for 14 days.

The injection of glioma cells into the animals causes a growth of tumors. The growth of the tumors was examined by measuring two diameters along two perpendicular axes. The true tumor diameter was estimated as the diameter minus 0.5 mm (which is the thickness of the skin). Tumor area (A) was calculated by multiplying the two true diameters and tumor volume was calculated by the formula: π/6×A3/2×0.67. The obtained tumor volumes are shown in the following table:

| Day | Tumor volume in mm³ | |
| --- | --- | --- |
| | $IP_3$ treatment | Control |
| 0 | 0 | 0 |
| 10 | 115 | 230 |
| 13 | 270 | 580 |
| 15 | 620 | 1190 |
| 17 | 880 | 2230 |
| 20 | 2420 | 4270 |

The results show a very marked effect of $IP_3$ to counteract by mechanisms as discussed above the growth of tumor tissue induced by glioma cells.

EXAMPLE 3

In the procedure similar to the one described in example 2, prostate tumor growth was induced by subcutanous injection of a specific cell type to mice. One group of animals received $IP_3$ via osmotic minipumps, while another group of animals served as a control. The tumor growth was examined and the tumor volume is shown in the following table:

| Day | Tumor volume in mm³ | |
| --- | --- | --- |
| | $IP_3$-treatment | Control |
| 0 | 0 | 0 |
| 7 | 36 | 52 |
| 10 | 62 | 130 |
| 17 | 51 | 481 |
| 24 | 95 | 638 |

| Day | Tumor volume in mm³ (continued) | |
| --- | --- | --- |
| | $IP_3$-treatment | Control |
| 28 | 171 | 1016 |
| 35 | 215 | 1132 |

In this example administration of $IP_3$ reduced the growth of prostate tumor tissue in a significant way.

EXAMPLE 4

Lewis lung carcinoma cells (ATCC CRL-1642) were grown as a suspension culture in a medium with 4.5 g/l of glucose with 10% heat inactivated bovine serum in a 5% $CO_2$ humidified atmosphere at 37° C. The cells were subcultured by diluting cell suspensions 1:6. After harvesting by centrifugation and resuspension, the cells were counted in a counting chamber. The cells were resuspended with medium to a concentration of 10 million cells/ml.

Ten male specific pathogen free mice at an age of 6 weeks were maintained in autoclaved caves with filter tops in a barrier unit equipped with HEPA filters. Autoclaved bedding, irradiated feed and sterile filtered water were used. The temperature and humidity were kept constant (22±2° C., 65±5% RH).

To each animal 0.1 ml of the cell suspension was inoculated subcutanousely in the right flank at day 0. After 15 days, osmotic minipumps (ALZET) were surgically placed subcutaneously into 5 animals while another 5 animals, sham operated, served as a control group.

Each minipump contained 226 μl of a solution of 0.4 g/ml of the sodium salt of 1-D-myo-inositol-1.2.6-trisphosphate ($IP_3$). The minipumps gave a continous dosage of $IP_3$ for 6 days.

The injection of lung carcinoma cells causes a formation of tumors and angiogenesis in lung tissue. The weight of the lungs after the experiment is considered as a measurement of the amount of tumor tissue is formed. In the sham operated animals, the mean lung weight was 0.312 g while the animals treated with $IP_3$ has a mean lung weight of 0.198 g. Furthermore, histological examination showed lower angiogenesis in the animals treated with $IP_3$. Thus the treatment with $IP_3$ reduces the tumor tissue and diminishes angiogenesis.

What is claimed is:

1. A method of treating angiogenesis in tumor tissues sensitive to the compound D-myo-inositol-1,2,6-trisphosphate consisting of administering to a mammal in need thereof, an effective amount of D-myo-inositol-1,2,6-trisphosphate or a pharmaceutically acceptable salt thereof.

2. A method according to claim 1 wherein the tumor tissue is a glioma tissue.

3. A method according to claim 1 wherein the tumor tissue is a prostate tumor tissue.

4. A method according to claim 1 wherein the tumor tissue is a lung carcinoma tissue.

5. A method according to claim 1 wherein said pharmaceutically acceptable salt is a salt of sodium, potassium, calcium, zinc or a combination thereof.

6. A method according to claim 1 wherein said D-myo-inositol-1,2,6-trisphosphate or said pharmaceutically acceptable salt thereof is administered in a unit dosage form comprising tablets, granules, solutions or suspensions.

7. A method of treating tumor growth in tumor tissue sensitive to the compound D-myo-inositol-1,2,6- trisphosphate consisting of administering to a mammal in need thereof, an effective amount of D-myo-inositol-1,2,6-trisphosphate or a pharmaceutically acceptable salt thereof.

8. A method according to claim 7 wherein the tumor tissue is a glioma tissue.

9. A method according to claim 7 wherein the tumor tissue is a prostate tumor tissue.

10. A method according to claim 7 wherein the tumor tissue is a lung carcinoma tissue.

11. A method according to claim 7 wherein said pharmaceutically acceptable salt is a salt of sodium, potassium, calcium, zinc or a combination thereof.

12. A method according to claim 7 wherein said D-myo-inositol-1,2,6-trisphosphate or said pharmaceutically acceptable salt thereof is administered in a unit dosage form comprising tablets, granules, solutions or suspensions.

* * * * *